(12) United States Patent
Dos Santos et al.

(10) Patent No.: US 8,864,701 B2
(45) Date of Patent: Oct. 21, 2014

(54) IMPLANTABLE MEMS DEVICE AND METHOD

(75) Inventors: Cesario P. Dos Santos, Aliso Viejo, CA (US); Nicholas M. Gunn, Newport Beach, CA (US); Robert J. Sanchez, Jr., Oceanside, CA (US); Leslie A. Field, Portola Valley, CA (US); Chen Ning, Richmond, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 5 days.

(21) Appl. No.: 13/584,435

(22) Filed: Aug. 13, 2012

(65) Prior Publication Data

US 2014/0046439 A1 Feb. 13, 2014

(51) Int. Cl.
*A61M 5/00* (2006.01)

(52) U.S. Cl.
USPC ................................................. 604/9; 604/8

(58) Field of Classification Search
CPC .......... A61F 2/16; B32B 37/14; B32B 38/10; B32B 37/12
USPC .......... 604/9, 8; 623/6.22; 156/60, 250, 273.7
See application file for complete search history.

(56) References Cited

U.S. PATENT DOCUMENTS

| 2006/0036207 | A1 | 2/2006 | Koonmen et al. |
| 2010/0004639 | A1* | 1/2010 | Pang et al. ................ 604/891.1 |
| 2010/0168644 | A1* | 7/2010 | Brown .............................. 604/8 |
| 2011/0071458 | A1 | 3/2011 | Rickard |

FOREIGN PATENT DOCUMENTS

| DE | 4438201 A1 | 5/1996 |
| WO | WO 2013/090197 A1 | 6/2013 |

OTHER PUBLICATIONS

International Search Report and Written Opinion issued for PCT/US2013/054795 dated May 23, 2014, 14 pages.

* cited by examiner

*Primary Examiner* — Tatyana Zalukaeva
*Assistant Examiner* — Benedict L Hanrahan
(74) *Attorney, Agent, or Firm* — Haynes and Boone, LLP

(57) ABSTRACT

An implantable MEMS package for the treatment of an ocular condition is provided. The MEMS package includes an outer portion; an active portion attached to the outer portion, the active portion including a fluid regulating element having a moving element; and a fluidic channel at an interface of the outer portion and the active portion. The fluidic channel is formed in at least one of the outer and active portions and permits fluid communication from the MEMS package to the fluid regulating element. A method for forming a MEMS package as above is also provided. An ocular implant for treating glaucoma including an inlet tube for receiving aqueous humor; a MEMS package as above, coupled to the inlet tube; a control system to control the MEMS package; and an outlet tube for draining aqueous humor at a drainage location, is provided.

17 Claims, 11 Drawing Sheets

IMPLANTABLE MEMS DEVICE AND METHOD

BACKGROUND

Embodiments described herein relate to the field of intraocular implants for use in ophthalmic treatments. More particularly, embodiments described herein are related to the field of intraocular pressure (IOP) control systems, for use in ophthalmic treatments.

Glaucoma, a group of eye diseases affecting the retina and optic nerve, is one of the leading causes of blindness worldwide. Most forms of glaucoma result when the intraocular pressure (IOP) increases above normal for prolonged periods of time. IOP can increase due to high resistance to the drainage of the aqueous humor relative to its production rate. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Also shown in FIG. 1 are posterior chamber 170 and anterior chamber 175. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from anterior chamber 175 to a drainage site outside the eye, relieving pressure in the eye and thus lowering IOP. These devices are generally passive devices and do not provide a smart, interactive control of the amount of flow through the drainage tube. In addition, fluid filled blebs frequently develop at the drainage site. The development of the bleb typically includes fibrosis, which leads to increased flow resistance; it is generally the case that this resistance increases over time. The development and progression of fibrosis reduces or eliminates flow from anterior chamber 175, reducing the capacity of the drainage device to affect IOP. While many implanted drainage devices incorporate micro-electro-mechanic systems (MEMS), state-of-the-art devices have separate tubing sets and components to operate as fluidic routes. The tubing sets are crudely glued onto the active MEMS device using adapters and complex clamping structures to connect the fluidic parts.

Therefore, there is a need for simple and compact MEMS packages to provide fluidic paths in implanted devices for IOP control.

SUMMARY

According to embodiments disclosed herein an implantable micro-electromechanical system (MEMS) package for the treatment of an ocular condition may include: an outer portion; an active portion attached to the outer portion, the active portion including a fluid regulating element having a moving element; and a fluidic channel at an interface of the outer portion and the active portion. In some embodiments the fluidic channel is formed in at least one of the outer and active portions and configured to permit fluid communication from an edge of the MEMS package to the fluid regulating element.

According to some embodiments, a method for forming a micro-electromechanical system (MEMS) package, may include providing a cover substrate having a plurality of fluidic channels; providing a MEMS device in an active substrate, the MEMS device configured to regulate flow through the package; applying an adhesive layer on one of the cover substrate and the active substrate; and bonding the cover substrate to the active substrate to form a stack layer.

According to some embodiments an ocular implant for treating glaucoma may include an inlet tube for receiving aqueous humor; a MEMS package coupled to the inlet tube; a control system to control the MEMS package; and an outlet tube for draining aqueous humor at a drainage location, the outlet tube coupled to the MEMS package. In some embodiments the MEMS package includes an outer portion; an active portion attached to the outer portion, the active portion including a fluid regulating element having a moving element; and a fluidic channel at an interface of the outer portion and the active portion. In some embodiments the fluidic channel is formed in at least one of the outer and active portions and is configured to permit fluid communication from one of the inlet tube and the optional outlet tube to the fluid regulating element.

These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

Figure 1:
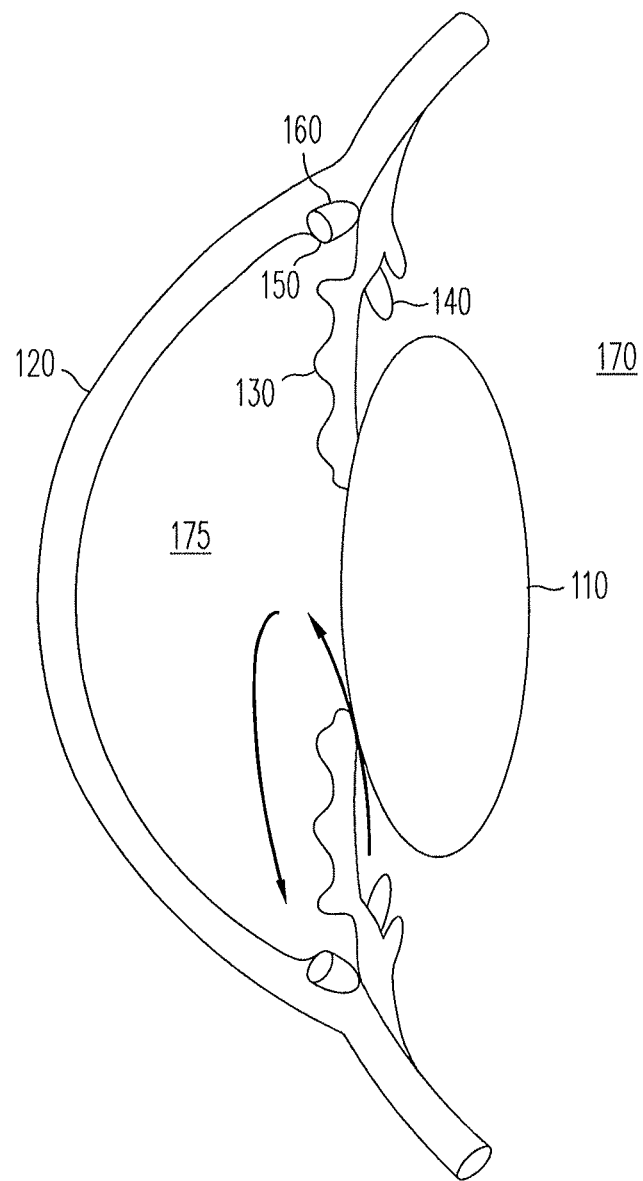
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to a method and system for providing fluidic connections to an implantable device used to control IOP. According to some embodiments, IOP is measured with an atmospheric reference pressure taken at a "dry" subconjunctiva location. A "dry" location, as used herein, is a location spaced apart from an aqueous humor drainage site such that it is not influenced by the wetter tissue at the drainage site. The systems and methods disclosed herein may enable fluid flow from anterior chamber 175 to an outer portion of the eye in implanted devices using active MEMS devices. According to some embodiments, a MEMS device may be directly bonded to an interface chip including fluidic channels etched from silicon or glass forming a MEMS package. The packaging of a MEMS device into an interface chip including the fluidic channels may be performed at the wafer fabrication stage, according to some embodiments. Thus, the time to manufacture a testable implant setup is reduced and may be scaled for production rapidly, reducing the margin of error compared to state-of-the-art implant devices.

Figure 2:
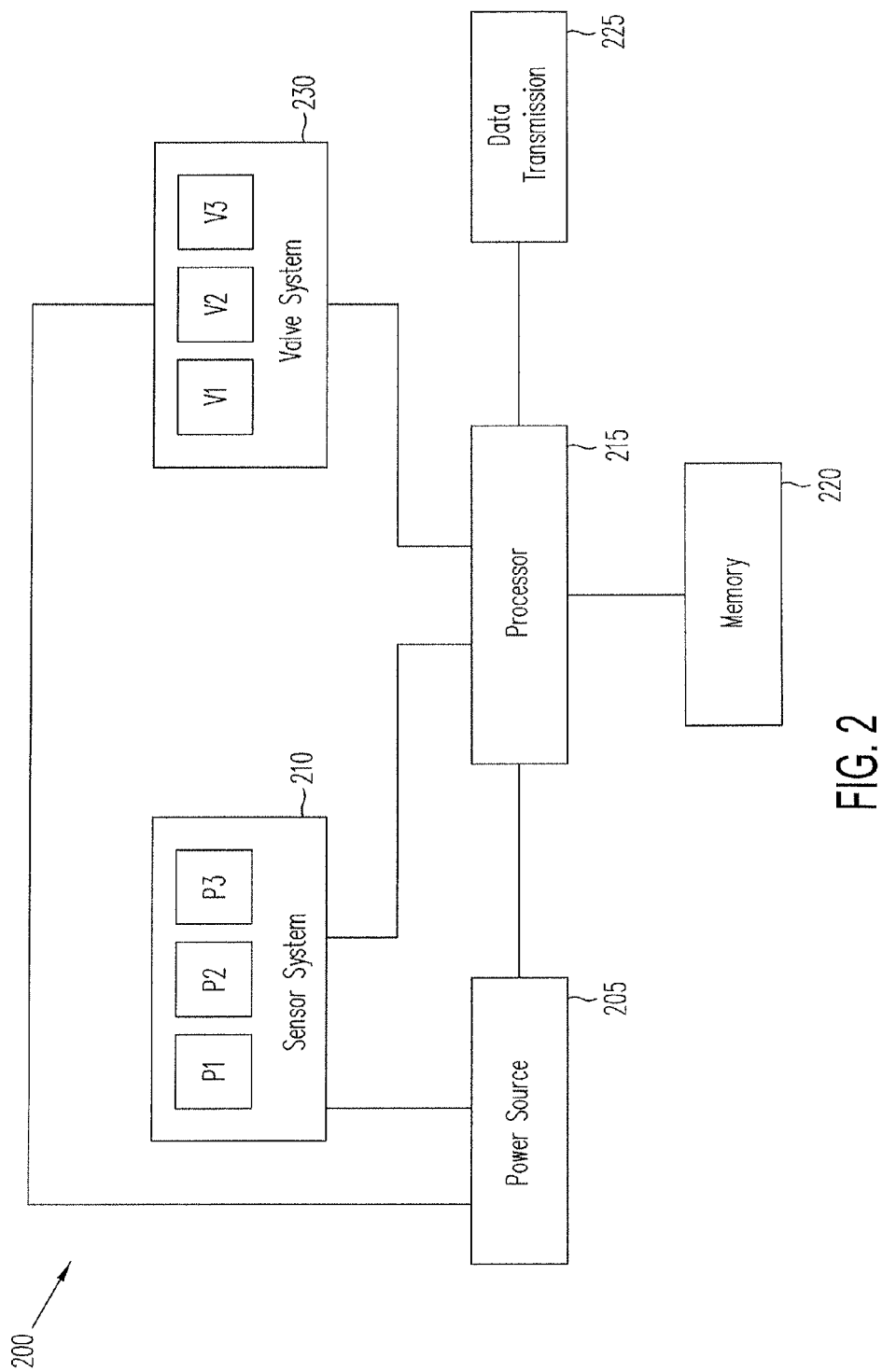
FIG. 2 is a block diagram of an exemplary IOP control system, according to some embodiments.

FIG. 2 is a block diagram of an exemplary IOP control system 200, according to some embodiments. IOP control system 200 is configured in a manner that provides IOP pressure control, but this embodiment also regulates and controls bleb pressures, reducing complications arising from surgical implant glaucoma devices. In FIG. 2, IOP control system 200 includes a power source 205, an IOP sensor system 210, a processor 215, a memory 220, a data transmission module 225, and a valve system 230.

In some embodiments processor 215 is an integrated circuit with power, input, and output pins capable of performing logic functions. Processor 215 may be a controller that controls different components performing different functions. Memory 220 may be a semiconductor memory that interfaces with processor 215. In one example, processor 215 can write data and commands to and read data and commands from memory 220. For example, processor 215 can be configured to read data from sensor system 210 and write that data to memory 220. In this manner, a series of sensed or calculated IOP readings can be stored in memory 220. Processor 215 is also capable of performing other basic memory functions, such as erasing or overwriting memory 220, detecting when memory 220 is full, and other common functions associated with managing semiconductor memory.

Valve system 230 may include a passive valve, a pressure driven valve, an electronically controlled valve, or other type of valve controlling flow of aqueous humor through IOP control system 200. Valve system 230 may include any number of valves and valve types, in combination. Some embodiments also include one or more pumping systems cooperating with one or more valves in valve system 230, providing pressure relief when needed. Pumps are also contemplated and may form a part of the valve system, or a separate part of the IOP control system 200.

As shown in FIG. 2, IOP sensor system 210 includes pressure sensors P1, P2, and P3. These pressure sensors can be any type of pressure sensors suitable for implantation in the eye. Each of pressure sensors P1, P2, and P3 may be the same type of pressure sensor, or they may be different types of pressure sensors.

Generally, IOP is a gauge pressure reading—the difference between the absolute pressure in the eye (e.g. as measured by sensor P1) and atmospheric pressure (e.g. as measured by the sensor P3). For example, in some embodiments sensor P1 may take pressure readings for anterior chamber 175 (as measured by sensor P1), sensor P2 may take pressure readings for a drainage location (as measured by sensor P2) and atmospheric pressure in the vicinity of the eye (as measured by the sensor P3). The pressure readings of sensors P1, P2, and P3 and the results of any calculations can be stored in memory 220 by processor 215. They can later be read from memory 220 so that actual IOP over time can be interpreted by a physician.

Readings from pressure sensors P1, P2, and P3 can be used to control the flow rate through valve system 230. Valve system 230 may be controlled by microprocessor 215 based on input data received from sensor system 210. A desired pressure differential (corresponding to a desired flow rate) can be maintained by controlling the operation of the valve system 230. Likewise, various intraocular pressure parameters, such as, by way of non-limiting example, a desired IOP, an IOP change rate, and/or a bleb pressure may be controlled by controlling the operation of valve system 230.

Data transmission module 225 transmits information from the implanted IOP control system 200 to the exterior of IOP control system 200, according to some embodiments. Data transmission module 225 may include a radio-frequency (RF) device using a digital data protocol. In such embodiments, an external unit may be configured to verify the readings from sensor system 210 indicating the pressure at the dry subconjunctiva under IOP control system 200.

Figure 3:
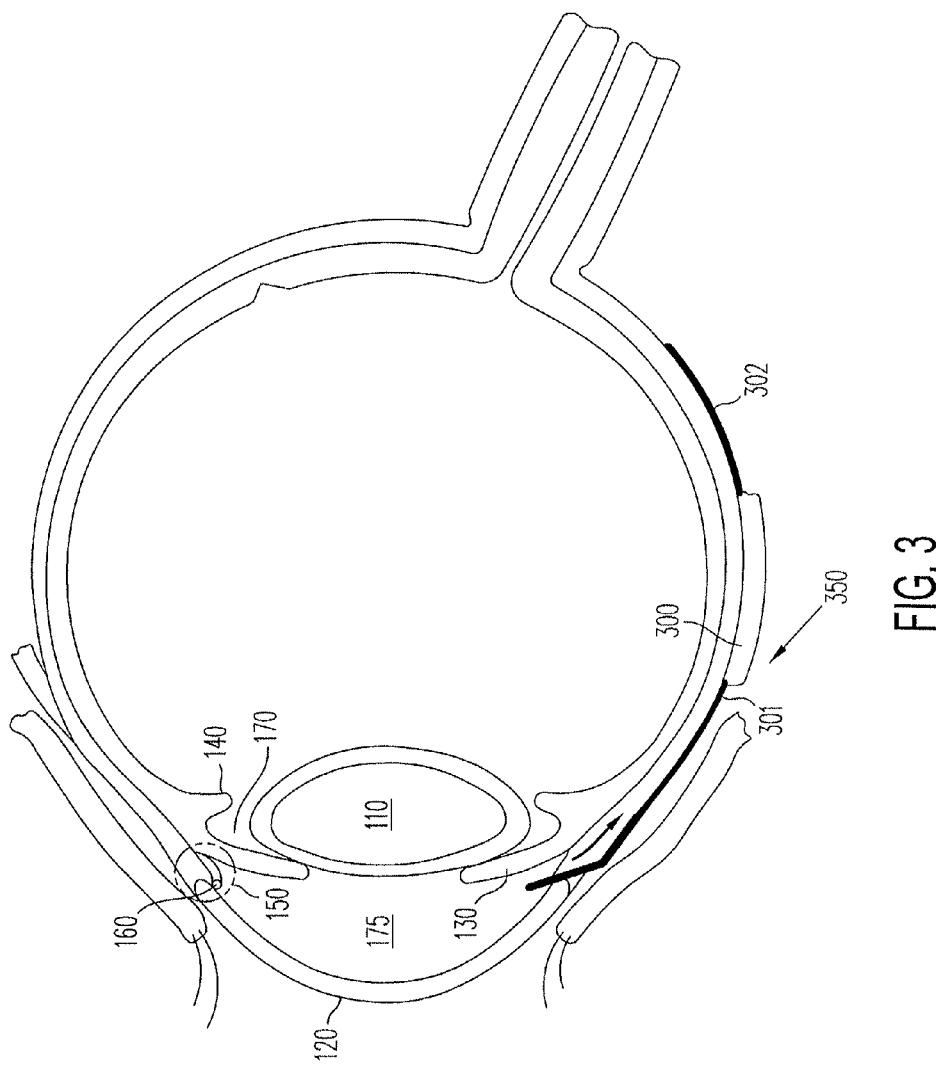
FIG. 3 is a schematic diagram of an ocular implant that carries the IOP control system of FIG. 2, according to some embodiments.

FIG. 3 is a schematic diagram of an ocular implant or drainage device 350 that carries IOP control system 200, according to some embodiments. Drainage device 350 includes a plate 300, an inlet tube 301, and an optional outlet tube 302. Plate 300 is arranged to carry components of IOP control system 200 shown in FIG. 2. For example, plate 300 may include power source 205, elements of sensor system 210, processor 215, memory 220, data transmission module 225, and valve system 230.

Plate 300 is configured to fit at least partially within the subconjunctival space and its dimensions may vary. In some embodiments plate 300 is between about 15 mm×12 mm to about 30 mm×15 mm in area, with a thickness less than about 2 mm, and preferably less than about 1.5 mm. Plate 300 may be formed in a curved shape to the radius of the eye globe (about 0.5 inches). In some embodiments, plate 300 may be rigid and preformed with a curvature suitable to substantially conform to the eye globe or it may be flexible and able to flex to conform to the eye globe. Some embodiments are small enough that conforming to the eye globe provides little benefit in comfort or implantation technique. The above dimensions are exemplary only, and other sizes and arrangements are contemplated herein.

Inlet tube 301 extends from an anterior side of plate 300 and extends into anterior chamber 175. Inlet tube 301 includes an open end and a lumen that extends into an active portion inside plate 300. The active portion inside plate 300 may include IOP control system 200, according to some embodiments. Outlet tube 302 is coupled to the active portion inside plate 300 and includes an open end and a lumen extending to an outer portion of the eye. According to some embodiments, aqueous humor from anterior chamber 175 flows through inlet tube 301 and exits about plate 300 or through optional outlet tube 302, to a drainage site. In some embodiments, the flow of aqueous humor through drainage device 350 is controlled by the active portion inside plate 300. The drainage site may be around the plate or at the open end of outlet tube 302 which may be proximate to plate 300.

In some embodiments, inlet tube 301 and optional outlet tube 302 drain aqueous humor from the anterior chamber 175 of the eye to the drainage site. Valve system 230 in IOP control system 200, included in plate 300, controls flow of aqueous humor through tubes 301 and 302. In some embodiments, pressure sensor P1 measures pressure at inlet tube 301, upstream from valve system 230 (in plate 300). In this manner, pressure sensor P1 measures pressure in anterior chamber 175.

Optional outlet tube 302 shunts fluid to a drainage location, which may be at any of numerous locations within the eye. In some embodiments, outlet tube 302 may shunt aqueous humor from anterior chamber 175 to the subconjunctival space, forming a bleb under the conjunctiva. Alternatively, outlet tube 302 may shunt aqueous humor from anterior chamber 175 to the subscleral space, forming a bleb under the sclera. In some embodiments, outlet tube 302 may shunt aqueous humor from anterior chamber 175 to the suprachoroidal space, the supraciliary space, the juxta-uveal space, or to the choroid, forming aqueous reservoirs to facilitate absorption in those respective locations. In some embodiments, outlet tube 302 shunts aqueous humor from anterior chamber 175 to Schlemm's canal, a collector channel in Schlemm's canal, or any of a number of different blood vessels like an episcleral vein. In some examples, outlet tube 302 even shunts aqueous humor from anterior chamber 175 to outside the conjunctiva. Each of the different anatomical locations to which aqueous humor is shunted is an example of a drainage location.

Figure 4:
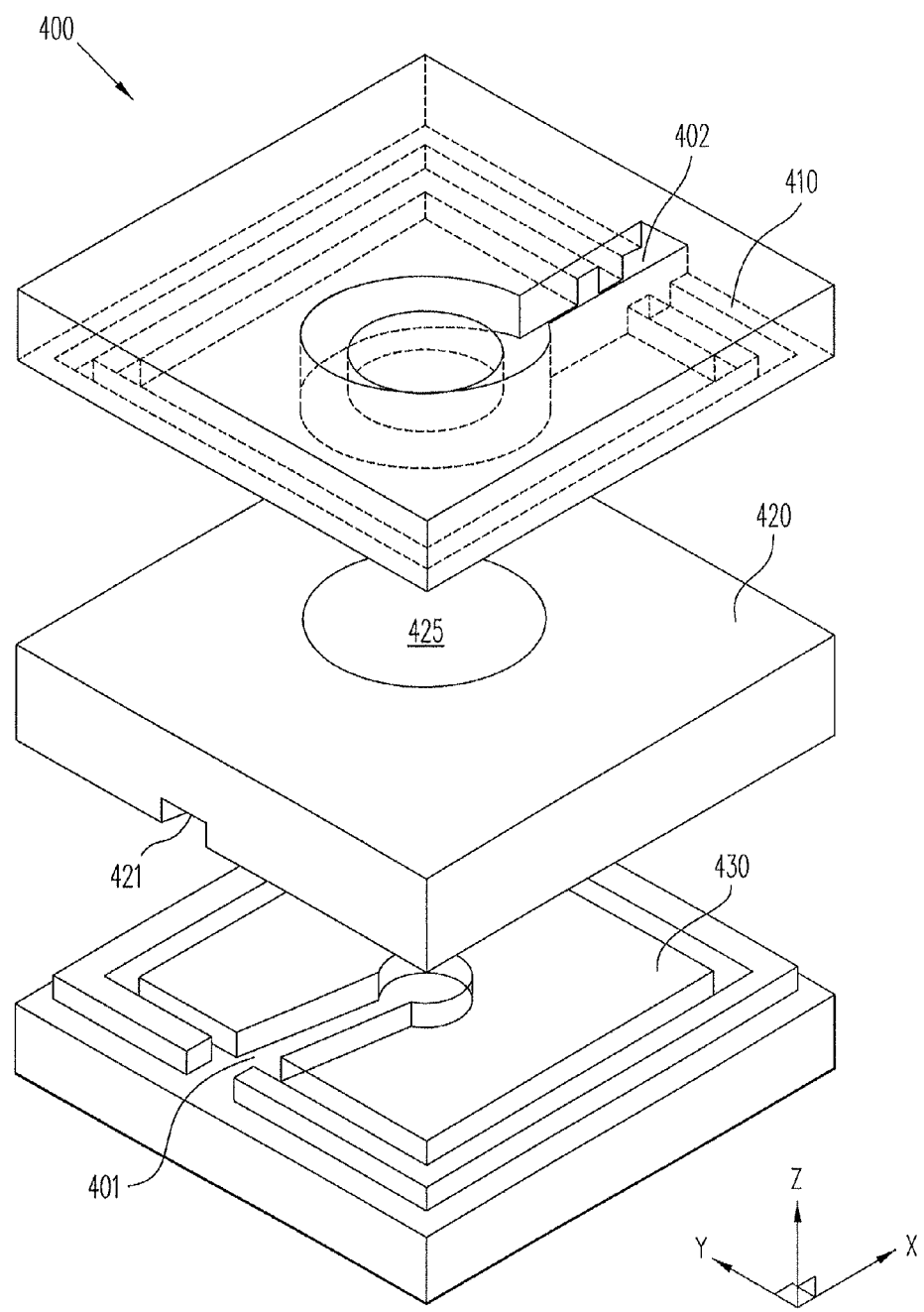
FIG. 4 shows a MEMS package with fluidic channels for an ocular implant, according to some embodiments.

FIG. 4 shows a MEMS package 400 with fluidic channels for ocular implant 350 in an exploded rendition, according to some embodiments. MEMS package 400 may be included inside or form a part of plate 300, described in detail above (cf. FIG. 3). MEMS package 400 includes an outer portion 410, and an outer portion 430, placed adjacent to either side of an active portion 420. FIG. 4 shows outer portion 410 on top and outer portion 430 at the bottom of active portion 420, for illustrative purposes. One of ordinary skill would recognize that the orientation of MEMS package 400 is not limiting and the position of outer portion 410 and of outer portion 430 relative to active portion 420 may be reversed, consistent with embodiments disclosed herein. Outer portion 410 includes a fluidic channel 402 that may be coupled to outlet tube 302, described in detail above (cf. FIG. 3). Outer portion 430 includes a fluidic channel 401 that may be coupled to inlet tube 301, described in detail above (cf. FIG. 3). According to some embodiments, outer portion 410 may be attached to outer portion 430 to form MEMS package 400.

For ease of reference, FIG. 4 includes a Cartesian coordinate system in three dimensions (3D). Hereinafter, embodiments consistent with the present disclosure are illustrated in relation to the 3D Cartesian coordinate system shown in FIG. 4. The choice of axes and the orientation of the 3D Cartesian coordinate system shown in FIG. 4 is arbitrary and for illustrative purposes only. One of ordinary skill will recognize that any orientation and any other labeling of the coordinate axes (X, Y, and Z) is possible, without limiting the scope of the present disclosure.

In some embodiments, MEMS package 400 is a flow-regulating device including an inlet and an outlet encapsulated by a layer of material such as glass, plastic, silicon, or a metal. The glass, plastic, silicon or metal layer forms an outer portion of MEMS package 400. An outer portion of MEMS package 400 may include outer portion 410, outer portion 430, or both. MEMS package 400 may be used to control TOP in the treatment of glaucoma patients. An active portion 420 of MEMS package 400 includes a MEMS device that may be formed on a silicon substrate. In some embodiments, active portion 420 includes a silicon substrate and other materials forming moving parts and electrical connections, as is well known to one of ordinary skill in the art of MEMS manufacturing. For example, in some embodiments consistent with the present disclosure, a MEMS device in active portion 420 may include multiple layers of MEMS activated components. Each of the multiple layers may include moving components and electrical connections, transistors, gates, and other elements common to semiconductor circuit manufacturing. Moving components in active portion 420 may include valves, pistons, and membranes, among other examples. Furthermore, moving components in active portion 420 may be enclosed or separated by cavities, walls and conduits included in active portion 420.

In embodiments consistent with the present disclosure, MEMS package 400 is configured to generally regulate the flow rate between channel 401 and channel 402. It may be configured to increase the flow rate between channel 401 and 402 and it may, in addition to or as an alternate to, reduce the flow rate between channel 401 and channel 402. The operation of MEMS package 400 is controlled by processor circuit 215 according to some embodiments (cf. FIG. 2).

Active portion 420 includes a MEMS device 425 having a moving element and a cavity that couples fluidic channel 401 to fluidic channel 402. The moving element in MEMS device 425 controls the fluid flow between fluidic channels 401 and 402. In some embodiments, active portion 420 may be monolithically formed on a silicon substrate, including the moving part. MEMS device 425 controls fluid flow from fluidic channel 401 to fluidic channel 402. MEMS device 425 may be configured to allow 100% of the flow from channel 401 to pass through to channel 402. In some embodiments, MEMS device 425 may be configured to restrict the fluid flow from channel 401 to channel 402 from 100% to 0%, and to any desired proportion between 0% and 100%. MEMS device 425 may perform fluidic control by electrical circuitry receiving signals from a processor circuit such as processor 215, described in detail above (cf. FIG. 2). Thus, in some embodiments MEMS package 400 acts as a controllable valve, regulating flow of aqueous humor from inlet tube 301 to outlet tube 302 in ocular implant 350 when a pressure differential already exists between tube 301 and tube 302 (cf. FIG. 3). For example, MEMS package 400 may be included in any of valves V1, V2 and V3 in valve system 230, described in detail above (cf. FIG. 2). Further according to some embodiments, active portion 420 may act as a pump for creating a pressure differential and actively transferring fluid from channel 401 to channel 402, or from channel 402 to channel 401.

In some embodiments, two outer portions (e.g., 410 and 430) are bonded on either side of an active portion (420) in a 'sandwich' type configuration. In some embodiments, one outer portion may be bonded to the active portion to provide a MEMS package for fluidic control consistent with embodiments disclosed herein. In some embodiments, multiple outer portions 410 and 420 may be provided on a glass, plastic, silicon, or metal wafer according to standard wafer fabrication procedures such as etching, sandblasting, machining, or molding. A machining procedure may include laser ablation or any other standard tooling used for precise material removal.

In some embodiments, outer portions 410 and 430 may be formed of the same material, such as glass, silicon, metal, or plastic machined into a shape as illustrated in FIG. 4. In some embodiments, outer portions 410 and 430 may be formed by sandblasting, etching, or molding the material into a shape as illustrated in FIG. 4. According to some embodiments, MEMS package 400 is assembled by adhering outer portions 410 and 430 to active portion 420. For example, an adhesive such as glue may be placed in spots on contact surfaces between outer portions 410, 430, and active portion 420. Examples of glues that may be used in some embodiments are SU-8, an ultra-violet (UV) cured epoxy, or some other form of adhesive such as cyanoacrylate. As illustrated in FIG. 4, active portion 420 may include a channel 421 that is aligned with fluidic channel 401, such that the fluidic channel is formed by both 401 and 421 to optimize chip height. In some embodiments, channel 421 is etched on the substrate of active portion 420 (e.g. silicon). Thus, when active portion 420 is glued to outer portion 430, a taller inlet channel may be fit to an exterior tube, such as inlet tube 301. Channel 421 has an opening into MEMS device 425 on one end, and extends to an outer edge of MEMS package 400 on the other end. In some embodiments, channel 421 may be referred to as MEMS fluidic channel.

In embodiments of MEMS package 400 used for ocular implant 350, the shape of the stack may be approximately square, with a thickness smaller than the lateral dimensions of the stack (the thickness along the Z-axis in FIG. 4). For example, in some embodiments stack 400 may be a square having a lateral dimension of about 5 mm per side (X-Y axis in FIG. 4), and a thickness between 500 μm to 1 mm (Z-axis in FIG. 4).

Fabrication of multiple chips as MEMS package 400 may be performed by aligning two layers of glass, silicon, metal or plastic on either side of a silicon wafer and gluing the three elements together. One of the layers of glass, silicon, metal or plastic may include multiple portions formed as outer portion 410 and the other layer of glass may include multiple portions formed as outer portion 430. The silicon wafer may include multiple MEMS devices 425 with channels 421 etched in proper orientation. Alignment of the two layers of glass, silicon, metal or plastic to the silicon wafer and gluing the three elements together then results in multiple chips as MEMS package 400. Then, dicing the sandwiched structure provides multiple MEMS packages having identical properties. Dicing can be done by sawing the sandwiched structure along the edges of the aligned MEMS packages, or by laser ablation. One of ordinary skill may recognize that the materials used for making the layers sandwiched onto the silicon wafer as described above may be chosen according to the application, availability, cost, and ease of manufacturing.

In some embodiments, the layers used in the sandwich structure described above may be formed by traditional wafer manufacturing procedures. For example, a top layer may be formed by etching on a glass, silicon, metal or plastic wafer multiple portions such as outer portion 410. Likewise, a bottom layer may be formed by etching on a glass, silicon, metal or plastic wafer multiple portions as outer portion 430. Furthermore, in some embodiments a MEMS layer may be formed by traditional wafer manufacturing procedures to include multiple active portions as active portion 420 on a silicon wafer. The alignment of the top layer, the bottom layer, and the MEMS layer may be performed using traditional wafer manufacturing procedures, such as alignment features and indicators in each of the layers, formed specifically for alignment purposes. An alignment feature as used in some embodiments may be a tongue, a groove, or a similar mark formed on a wafer substrate. Thus, embodiments of a MEMS package as disclosed herein are easily manufactured on a large scale, reducing costs and error.

Figure 5:
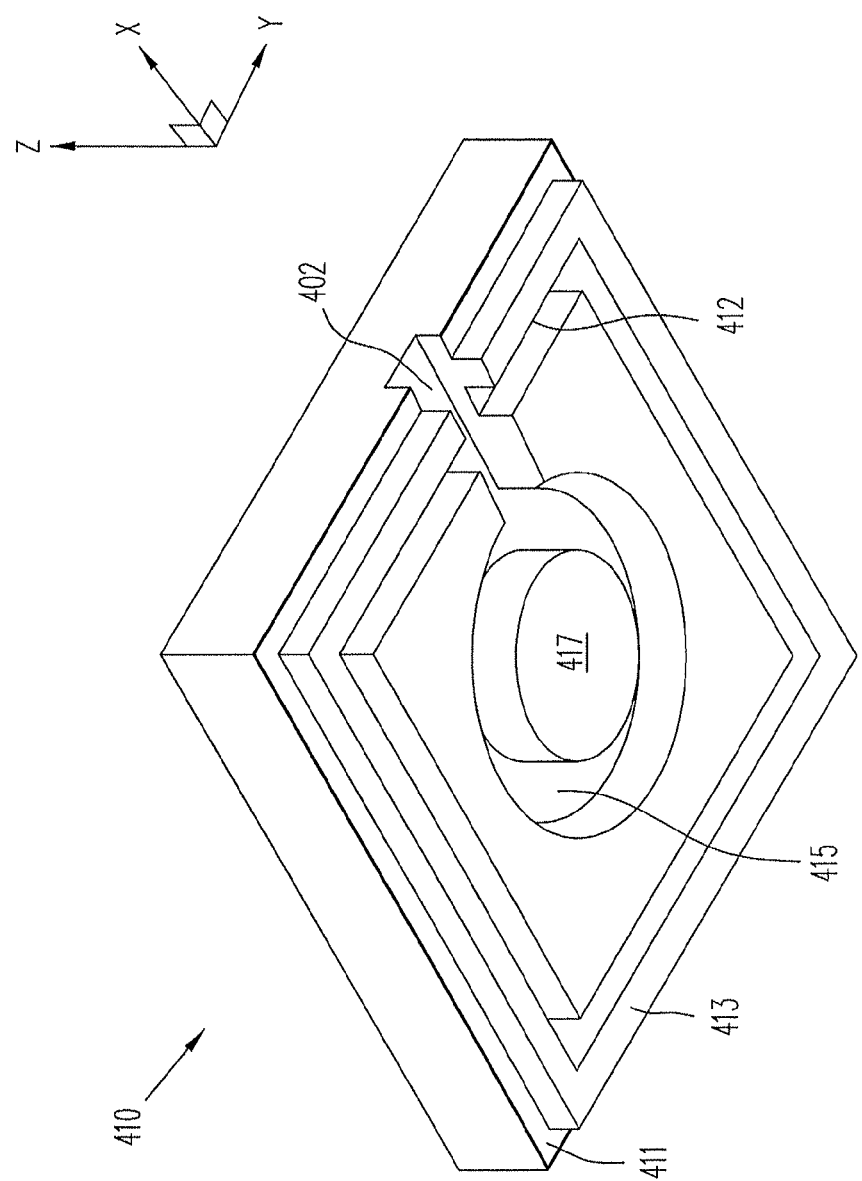
FIG. 5 shows a partial perspective view of an outer portion of a MEMS package with fluidic channels for an ocular implant, according to some embodiments.

FIG. 5 shows a partial perspective view of outer portion 410 of MEMS package 400 with fluidic channels for ocular implant 350, according to some exemplary embodiments. FIG. 5 illustrates fluidic channel 402, described in detail above (cf. FIG. 4), an exterior trench 411 and an interior trench 412. Exterior trench 411 and interior trench 412 form a rim 413 in the space between the trenches. Rim 413 may receive on its surface a glue that holds outer portion 410 together with active portion 420 in MEMS package 400. FIG. 5 also illustrates interior fluidic channel 415, and profile element 417.

When outer portion 410 is pressed against active portion 420 (cf. FIG. 4), excess glue from the surface of rim 413 may overflow into trenches 411 and 412. Thus, in some embodiments trenches 411 and 412 serve as glue overflow reservoirs. Trenches 411 and 412 prevent the formation of glue droplets protruding out of the periphery of MEMS package 400, or the overflow of excess glue into fluidic channels 401, 402, or 415. According to some embodiments, profile element 417 in outer portion 410 may include a portion of glue on its surface. In such embodiments, it may be desirable to include a circular trench around a center of profile element 417, so that excess glue may overflow into the trench when outer portion 410 is pressed against active portion 420.

Figure 6:
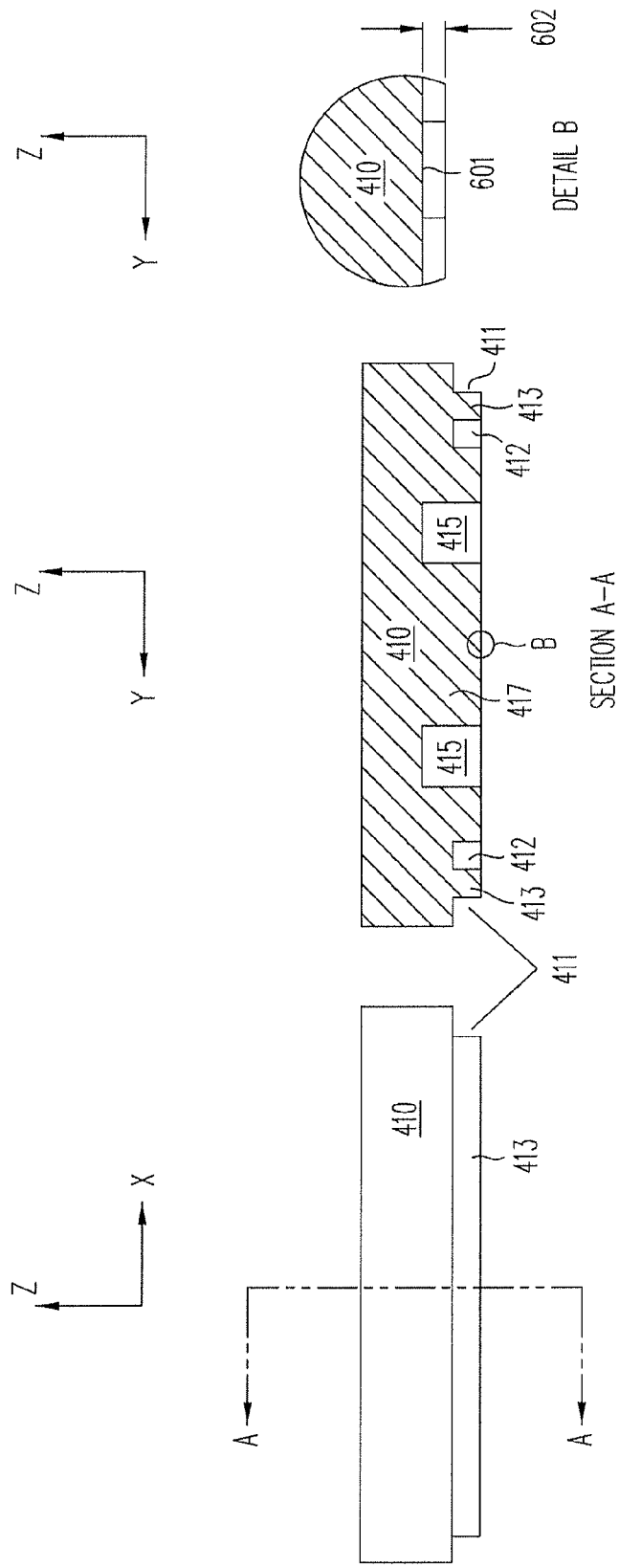
FIG. 6A shows a partial side view of an outer portion of a MEMS package for an ocular implant with fluidic channels, according to some embodiments.
FIG. 6B shows a partial cross section of an outer portion of a MEMS package for an ocular implant with fluidic channels, according to some embodiments.
FIG. 6C shows a detail in a cross section of an outer portion of a MEMS package for an ocular implant with fluidic channels, according to some embodiments.

FIG. 6A shows a partial side view of outer portion 410 of MEMS package 400 with fluidic channels for ocular implant 350, according to some embodiments. The edge of rim 413 is visible in FIG. 6A, including a portion of exterior trench 411. In some embodiments, the thickness of outer portion 410 may be less than 1 mm (along the Z-axis). For example, in some embodiments outer portion may be a few 100's of microns thick, such as anywhere from 100 to 200 or 300 μm.

FIG. 6B shows a partial cross section of outer portion 410 of MEMS package 400 with fluidic channels for ocular implant 350, according to some embodiments. FIG. 6B shows a cross section along the segment AA in FIG. 6A. FIG. 6B shows interior trench 412, exterior trench 411, rim 413, interior channel 415, and profile element 417.

FIG. 6C shows a detail B in a cross section of outer portion 410 of MEMS package 400 with fluidic channels for ocular implant 350, according to some embodiments. Glue layer 601 having a thickness 602 is placed on at least certain elements forming outer portion 410, such as profile element 417. In some embodiments, outer portion 410 is bonded to active portion 420 through the bottom surface shown in FIGS. 6A-6C. Thus, a glue layer 601 may be formed on the face of every element in outer portion 410 forming the bottom surface such as rim 413 and optionally profile element 417. In some embodiments, the thickness of glue layer 601 may be about 100 μm when outer portion is glued to active portion 420.

Figure 7:
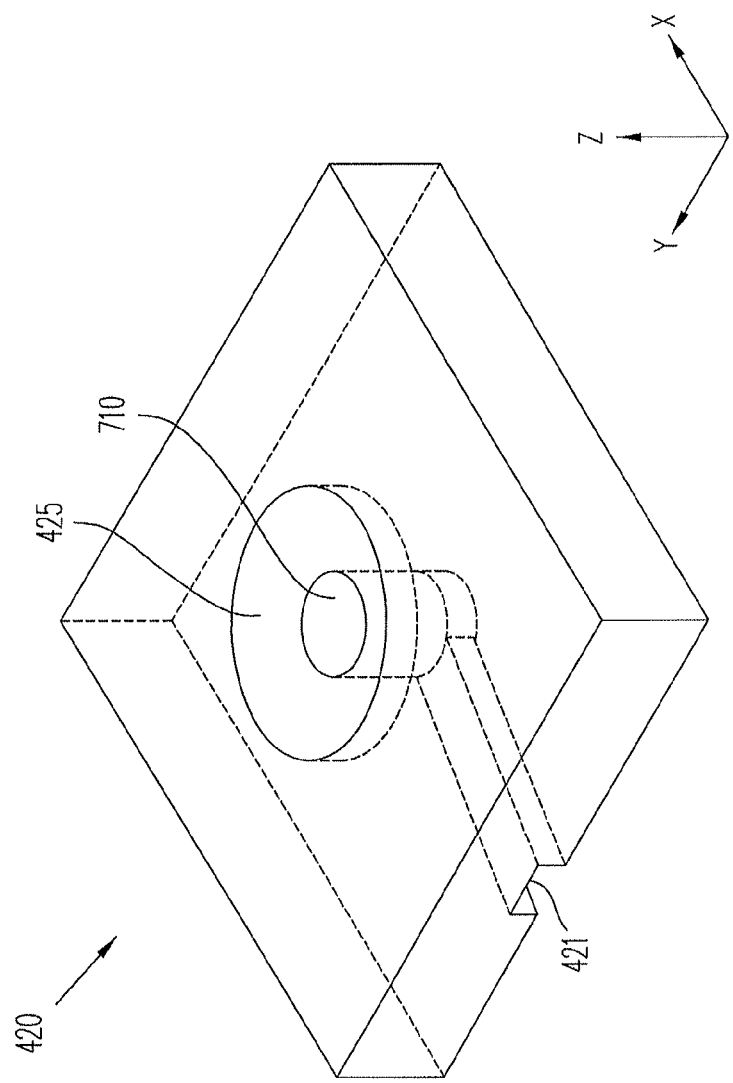
FIG. 7 shows a partial perspective view of an active portion of a MEMS package for an ocular implant with fluidic channels, according to some embodiments.

FIG. 7 shows a partial perspective view of active portion 420 of MEMS package 400 with fluidic channels for ocular implant 350, according to some embodiments. MEMS device 425 includes cavity 710. Active portion 420 may include a channel 421 etched into the substrate, to fit onto channel 401. In some embodiments, channel 421 may be precisely aligned with channel 401 of outer portion 410 after bonding the two portions together. Other elements in MEMS device 425 may be aligned with either outer portion 410 or outer portion 430.

Figure 8:
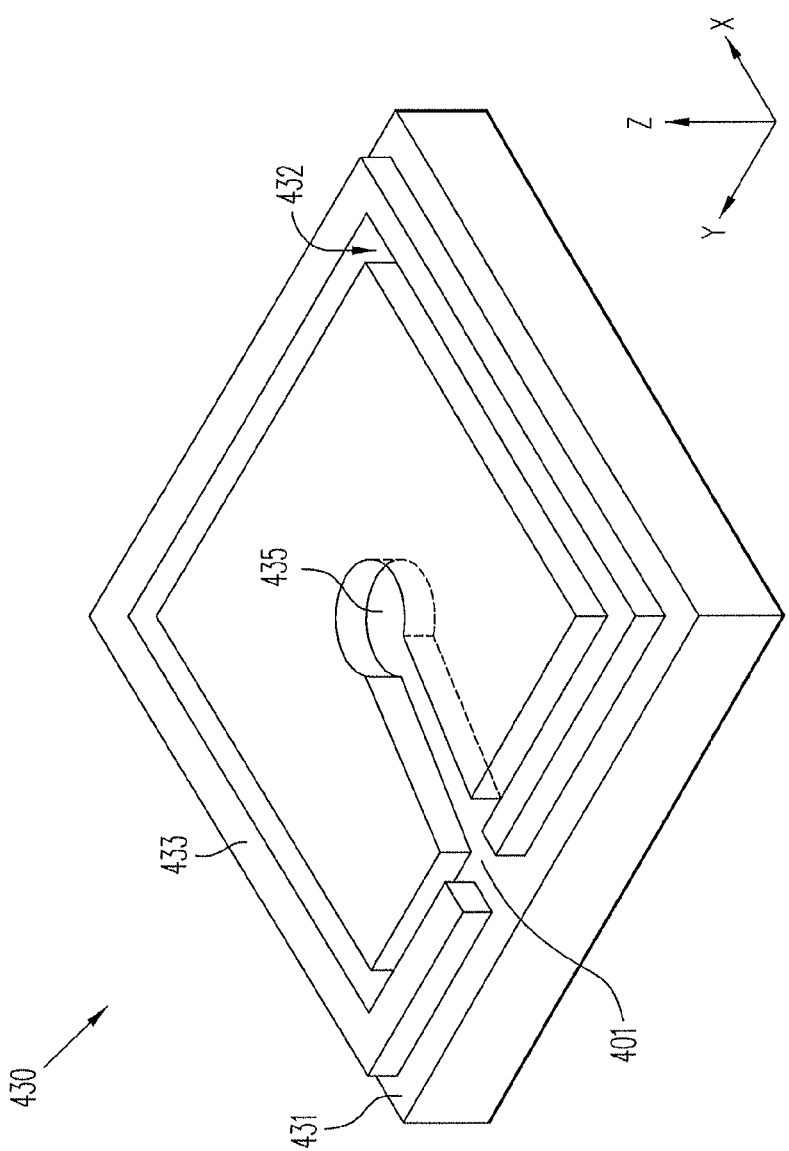
FIG. 8 shows a partial perspective view of an outer portion of a MEMS package for an ocular implant with fluidic channels, according to some embodiments.

FIG. 8 shows a partial perspective view of outer portion 430 of MEMS package 400 with fluidic channels for ocular implant 350, according to some embodiments. FIG. 8 illustrates fluidic channel 401, described in detail above (cf. FIG. 4). Also illustrated in FIG. 8 is exterior trench 431, interior trench 432, rim 433, and cavity 435. Trenches 431 and 432 may be as trenches 411 and 412 in outer portion 410 described in detail above (cf. FIG. 5), and serve the same purpose. Thus, in some embodiments a glue may be placed on rim 433 in order to assemble together outer portion 430 and active portion 420. Trenches 431 and 432 may serve as excess flow recipients for the glue, as active portion 420 is pressed onto outer portion 430.

Figure 9:
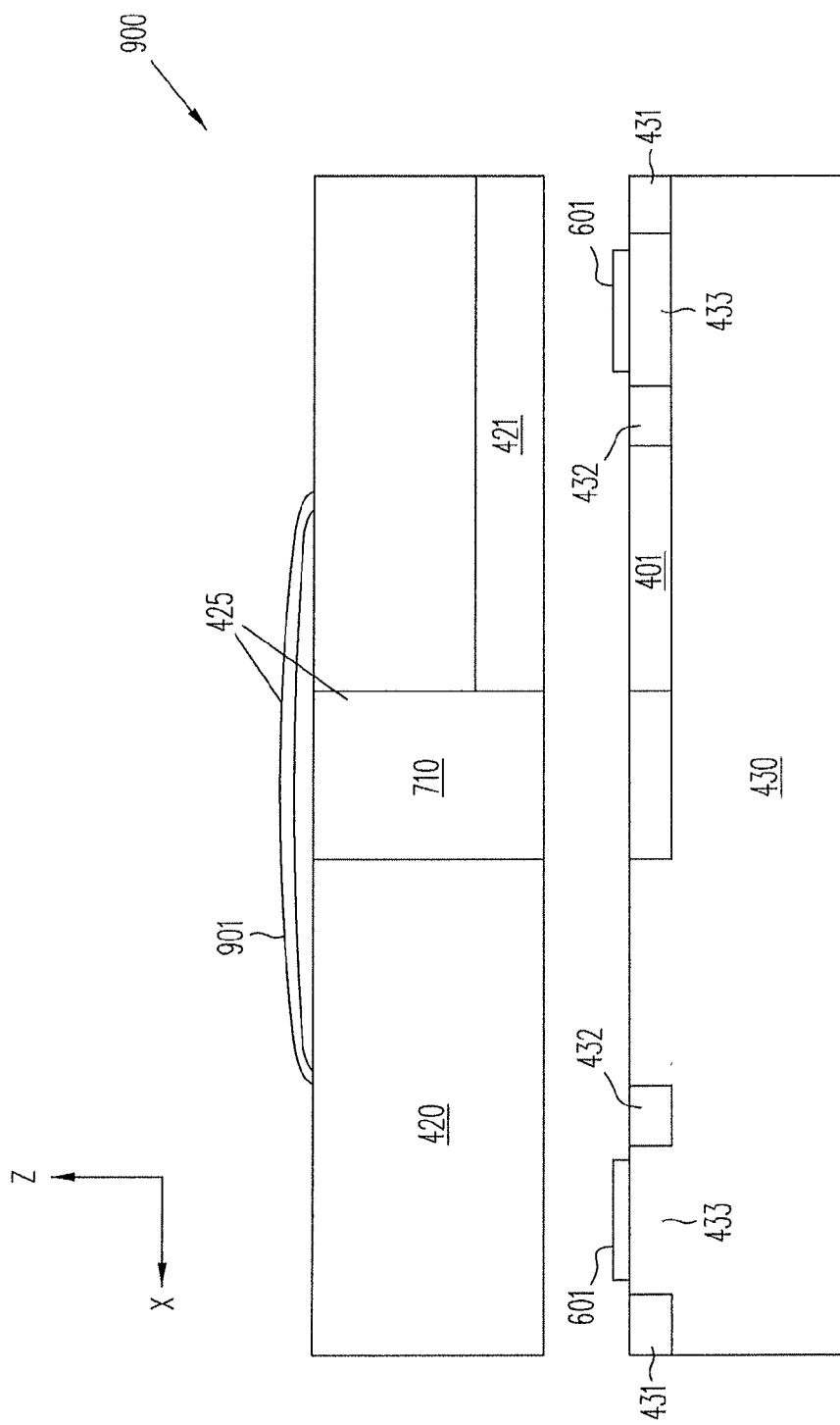
FIG. 9 shows a partial side view of a MEMS package for an ocular implant with fluidic channels, according to some embodiments.

FIG. 9 shows a partial side view of MEMS package 900 with fluidic channels for ocular implant 350, according to some embodiments. MEMS package 900 includes active portion 420 mated to outer portion 430. FIG. 9 illustrates fluidic channel 421 aligned with fluidic channel 401. According to some embodiments, an inlet tube such as tube 301 may be fluidically coupled to MEMS package 900 through the space formed between channels 401 and 421. MEMS device 425 in FIG. 9 includes a moving element which is a membrane 901, and a cavity 710. Glue or any other adhesive layer 601 is placed on the surface of rim 433 for bonding outer portion 430 with active portion 420. As outer portion 430 and active portion 420 are placed adjacent to one another, excess glue from layer 601 may overflow into trenches 431 and 432. For example, glue 601 may be SU-8 and the process of bonding outer portion 430 to active portion 420 may include applying pressure and heat to the stack. As pressure and heat are applied for bonding outer portion 430 to active portion 420, glue SU-8 may soften and extend, overflowing into trenches 431 and 432 and preventing the glue from spreading into fluidic channel 401 or cavity 710 in active portion 420.

In some embodiments, the position of membrane 901 relative to cavity 710 may determine the amount of flow through fluidic channel 421. Furthermore, in some embodiments the position and shape of membrane 901 may be determined by electro-magnetic signals provided by active elements in MEMS device 425. The electro-magnetic signals may be controlled by processor 215 upon receiving a signal from sensor system 210 (cf. FIG. 2).

Figure 10:
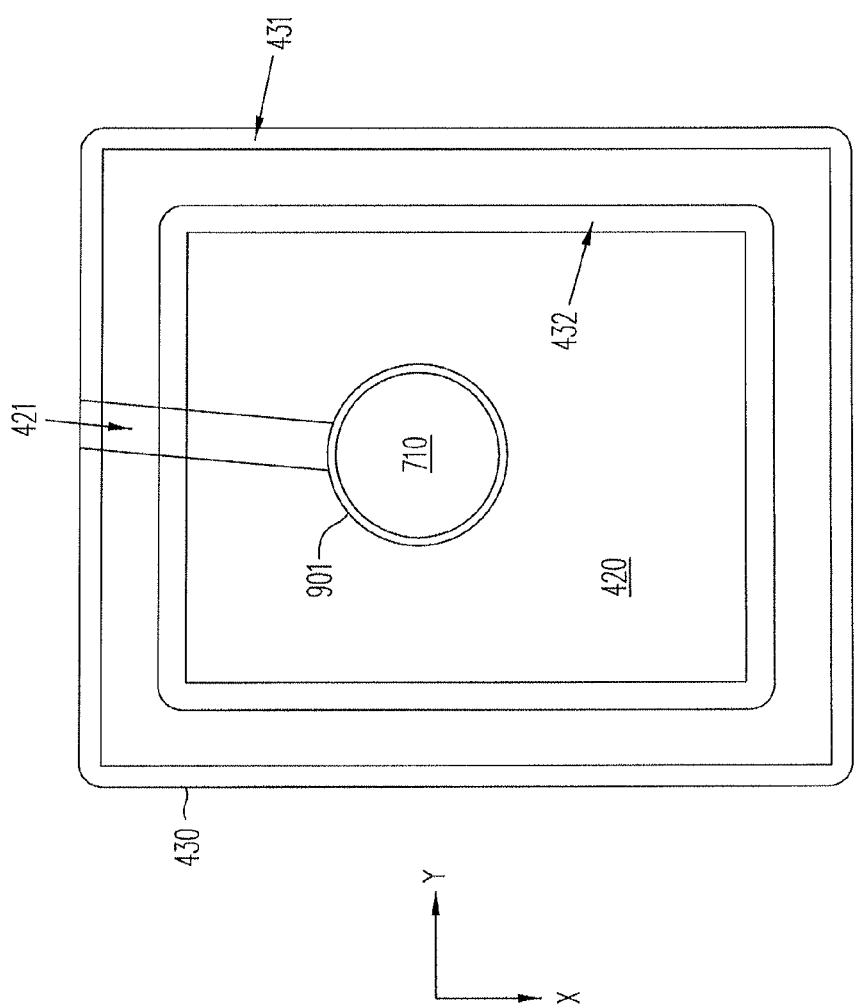
FIG. 10 shows a partial plan view of a MEMS package for an ocular implant with fluidic channels, according to some embodiments.

FIG. 10 shows a partial plan view of active portion 420 of MEMS package 900 with fluidic channels for ocular implant 350, according to some embodiments. FIG. 10 illustrates a plan view of the stack shown in FIG. 9. According to some embodiments, assembling active portion 420 together with outer portion 430 may include aligning the two portions in order that the orientation of fluidic channel 421 precisely matches the orientation of channel 401. In some embodiments portion 420 may be included in a wafer forming an active substrate, together with multiple other active portions. In some embodiments portion 430 may be included in a wafer forming a cover substrate, together with multiple other portions 430. The wafer including the active substrate may be aligned to the wafer including the cover substrate using alignment features on the wafer. Further according to some embodiments, trenches 431 and 432 may be used as alignment features. In some embodiments, rim 433 between trenches 431 and 433 may also be used as an alignment feature to assemble a MEMS package such as stack 900.

Figure 11:
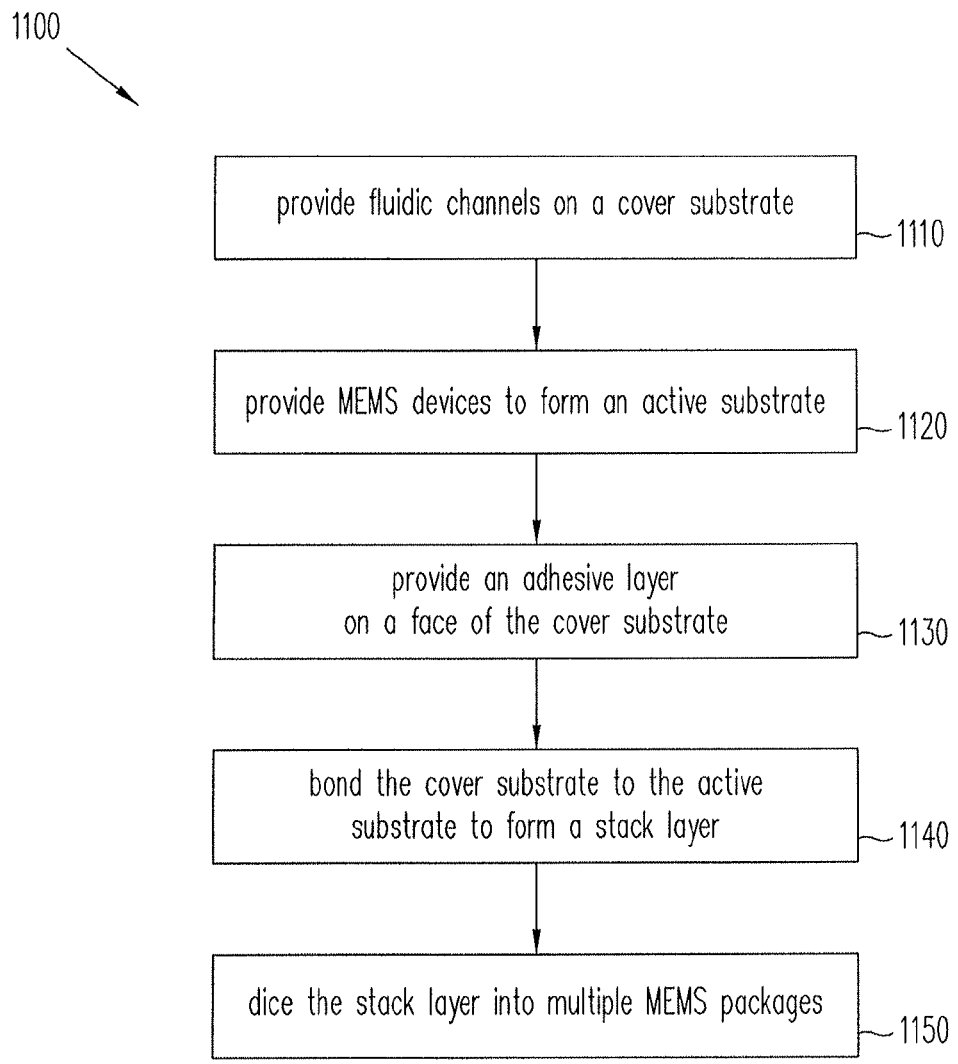
FIG. 11 shows a flowchart of a method for providing multiple MEMS packages for fluid flow regulation, according to some embodiments.

FIG. 11 shows a flowchart of a method 1100 for providing multiple MEMS packages for fluid regulation, according to some embodiments. Method 1100 includes step 1110 to provide fluidic channels on a cover substrate. In some embodiments, the cover substrate includes a glass, silicon, metal or plastic wafer. In some embodiments step 1110 includes etching fluidic channels on the glass, silicon, metal or plastic wafer using techniques such as chemical etching, sandblasting, machining, or molding. For example, some embodiments may use a mask and photolithography, or a mold, to perform step 1110. Fluidic channels etched on a cover substrate in step 1110 may be as channels 401, 402, and 415. Also, in step 1110 overflow trenches such as trenches 411 and 412 may be formed in the cover substrate. In some embodiments, step 1110 provides features and fluidic channels on a cover substrate including multiple outer portions such as portions 410 and 430 (cf. FIG. 4).

In some embodiments step 1110 may include forming two cover substrates as described above. A first cover substrate may include a plurality of outer portions 410, to be assembled on one side of active portion 420. A second cover substrate may include a plurality of outer portions 430, to be assembled on the opposite side of active portion 420. Thus, a MEMS package such as package 400 may be formed.

In step 1120, MEMS devices are provided on a substrate, forming an active substrate. In some embodiments, multiple MEMS devices such as circuit 425 may be formed on a silicon wafer, each MEMS device corresponding to a MEMS package such as package 400 (cf. FIG. 4). Step 1120 may include forming multiple layers of MEMS components for each MEMS device. Furthermore, step 1120 may include forming elements with different semiconductor materials, doping layers, vapor deposition or spin coating layers. Step 1120 may also include use of conducting materials such as copper, aluminum, silver, gold, platinum, tantalum, nickel, titanium, titanium oxide, and others. Materials used in the MEMS components may include: platinum, gold, titanium, titanium nitride, tantalum nitride, Parylene, SU-8, Silicon dioxide, and silicon nitride, among others. In preferred embodiments, the materials chosen to form an active substrate are biocompatible materials and suitable for implantation in a patient. Electrically conducting materials in step 1120 may be used to form electrical connections to active electronic components in the active substrate. Active electronic components may include transistors, capacitors, logical gates and integrated circuits.

In step 1130 an adhesive layer is provided on a face of the cover substrate. In some embodiments, the adhesive layer is spun onto the glass, silicon, metal or plastic wafer including the cover substrate. The adhesive layer may include a glue, such as SU-8 or any UV curable glue or epoxy. For example, step 1130 may include placing an amount of glue on an inner surface of the cover substrate and spinning the cover substrate until the amount of glue forms a layer having a uniform thickness on the inner surface of the cover substrate. Thus, a layer of glue may be placed on a surface of the wafer including multiple outer portions such as outer portion 410 or outer portion 430. A layer of glue may be as layer 601 (cf. FIGS. 6C and 9). The face of cover substrate selected for providing the glue layer may be an 'inner' face adjacent to the active substrate for bonding, as in step 1140.

In step 1140 the cover substrate of step 1110 is bonded to the active substrate of step 1120. According to some embodiments, in step 1140 the cover substrate having a glue layer and the active substrate are placed adjacent to each other while pressure and heat are applied to the combination to form a stack layer. In some embodiments two cover substrates are placed adjacent to either side of the active substrate and the stack layer forms a structure resembling a 'sandwich.' In embodiments where the adhesive layer includes a UV curable glue, step 1140 may include illuminating the combination of the at least one cover substrate and the active substrate with a UV light for a selected period of time.

In step 1150, the stack layer is diced and sliced into multiple MEMS packages such as MEMS package 400 (cf. FIG. 4). In some embodiments, step 1150 may be performed using a saw, or a laser ablation technique, or any other material ablation technique available. In embodiments where an active substrate is 'sandwiched' between a first cover substrate and a second cover substrate, the result of step 1150 may be multiple MEMS packages such as package 400 (cf. FIG. 4). In embodiments where an active substrate is bonded to a single cover substrate, the result of step 1150 may be multiple MEMS packages such as package 900 (cf. FIG. 9).

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. An implantable micro-electromechanical system (MEMS) package for the treatment of an ocular condition, comprising:
  a first layer having a first facing surface, the first layer forming an outer portion;
  a second layer having a second facing surface, the second layer being attached to the first layer in a manner forming an interface at the second facing surface and the first facing surface, the second layer forming an active portion comprising a fluid regulating element having a moving element;
  a fluidic channel formed within at least one of the first facing surface and the second facing surface at the interface of the first and second facing surfaces so that the fluidic channel is enclosed by a portion of both the first layer and the second layer, the fluidic channel extending from an edge of the MEMS package to the fluid regulating element of the second layer for drainage of fluid therethrough;
  wherein the second layer includes a third facing surface opposite the second facing surface, and wherein the fluidic passage is a first fluidic passage, the package comprising:
  a third layer having a fourth facing surface, the third layer being disposed so that the fourth facing surface faces and is attached to the third facing surface; and
  a second fluidic channel formed within at least one of the third facing surface and the fourth facing surface so that the second fluidic channel is formed and enclosed by a portion of both the third layer and the second layer, the second fluidic channel extending from the fluid regulating element of the second layer to a second edge of the MEMS package for drainage of fluid through the first fluidic passage to the fluid regulating element and for drainage of fluid through the second fluidic passage from the fluid regulating element and out of the MEMS package.

2. The package of claim 1, comprising a drainage tube in fluid communication with the fluidic channel, the drainage tube configured to drain aqueous humor within an eye of a patient.

3. The package of claim 1, comprising a control system operable to control the fluid regulating element to a position that permits increased flow or to a position that permits decreased flow at the active portion, or to a position that prevents flow.

4. The package of claim 3 wherein the control system comprises:
  a sensor system to measure pressure at different locations.

5. The package of claim 1 wherein the outer portion is bonded to the active portion by an adhesive layer placed on an inner surface of the outer portion.

6. The package of claim 5 comprising at least one trench in the inner surface of the outer portion for receiving excess flow of an adhesive from the adhesive layer.

7. The package of claim 5 wherein the adhesive layer comprises a glue selected from the group consisting of SU-8, an epoxy room temperature vulcanizing silicone, cyanoacrylate, and pressure sensitive adhesives.

8. The package of claim 1 further comprising a second outer portion attached to the active portion or to the first outer portion to form a stack layer.

9. An implantable micro-electromechanical system (MEMS) package for the treatment of an ocular condition, comprising:
  a first substrate portion having a first facing surface;
  a second substrate portion having a second facing surface, the second substrate portion being disposed so that the second facing surface faces and is attached to the first facing surface, the second substrate portion comprising a fluid regulating element configured to regulate the flow of drainage fluid when treating the ocular condition;
  a fluidic channel formed within at least one of the first facing surface and the second facing surface so that the fluidic channel is formed and enclosed by a portion of both the first substrate portion and the second substrate portion, the fluidic channel extending from an edge of the MEMS package to the fluid regulating element of the second layer for drainage of fluid therethrough;
  wherein the second substrate portion includes a third facing surface opposite the second facing surface, and wherein the fluidic passage is a first fluidic passage, the package comprising:

a third substrate portion having a fourth facing surface, the third substrate portion being disposed so that the fourth facing surface faces and is attached to the third facing surface; and a second fluidic channel formed within at least one of the third facing surface and the fourth facing surface so that the second fluidic channel is formed and enclosed by a portion of both the third substrate portion and the second substrate portion, the second fluidic channel extending from the fluid regulating element of the second layer to a second edge of the MEMS package for drainage of fluid through the first fluidic passage to the fluid regulating element and the drainage of fluid through the second fluidic passage from the fluid regulating element and out of the MEMS package.

10. The package of claim 9, comprising a drainage tube in fluid communication with the fluidic channel, the drainage tube configured to drain aqueous humor within an eye of a patient.

11. The package of claim 9, comprising a control system operable to control the fluid regulating element to a position that permits increased flow or to a position that permits decreased flow at the second substrate portion, or to a position that prevents flow.

12. The package of claim 11, wherein the control system comprises:

a sensor system to measure pressure at different locations.

13. The package of claim 9, wherein the first substrate portion is bonded to the second substrate portion by an adhesive layer placed on an inner surface of the first substrate portion.

14. The package of claim 13, comprising at least one trench in the first facing surface of the first substrate portion for receiving excess flow of an adhesive from the adhesive layer.

15. The package of claim 13, wherein the adhesive layer comprises a glue selected from the group consisting of SU-8, an epoxy room temperature vulcanizing silicone, cyanoacrylate, and pressure sensitive adhesives.

16. The package of claim 9, wherein the first substrate portion comprises a material selected from the group consisting of a silicon, a glass, a metal, and a plastic.

17. The package of claim 9, wherein the second substrate portion comprises a silicon wafer.

* * * * *